(12) United States Patent
Laustsen et al.

(10) Patent No.: US 6,582,606 B2
(45) Date of Patent: Jun. 24, 2003

(54) MICROFILTRATION USING ACTIVATED CARBON

(75) Inventors: Mads Aage Laustsen, Lyngby (DK); Søren Bo Nielsen, Værløse (DK); Sune Jakobsen, Værløse (DK); Kim Uhre Hansen, Kalundborg (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 09/860,927

(22) Filed: May 18, 2001

(65) Prior Publication Data
US 2002/0020668 A1 Feb. 21, 2002

Related U.S. Application Data
(60) Provisional application No. 60/206,539, filed on May 23, 2000.

(30) Foreign Application Priority Data
May 18, 2000 (DK) ......................................... 2000 00796

(51) Int. Cl.$^7$ ................................................ B01D 61/14
(52) U.S. Cl. ...................... 210/639; 210/651; 210/652; 210/774; 435/183; 530/412
(58) Field of Search ................. 210/636, 639, 210/650, 651, 767, 777, 778, 774, 791, 797, 798, 632, 652; 530/344, 412; 435/183, 261

(56) References Cited

U.S. PATENT DOCUMENTS

| | | | | |
|---|---|---|---|---|
| 4,610,792 A | | 9/1986 | Van Gils et al. | |
| 4,724,080 A | * | 2/1988 | Dau et al. | 210/651 |
| 4,909,942 A | * | 3/1990 | Sato et al. | 210/651 |
| 4,936,999 A | * | 6/1990 | Mattison et al. | 210/639 |
| 4,975,297 A | * | 12/1990 | Gresch | 210/798 |
| 5,262,053 A | | 11/1993 | Meier | |
| 5,728,559 A | * | 3/1998 | Nilsson et al. | 435/183 |
| 6,113,791 A | * | 9/2000 | Hartmann | 210/636 |

FOREIGN PATENT DOCUMENTS

| | | |
|---|---|---|
| DE | 4234392 A1 | 4/1994 |
| GB | 2 249 315 A | 5/1992 |
| WO | WO 89/00013 | 12/1989 |
| WO | WO 93/08702 | 5/1993 |

* cited by examiner

Primary Examiner—Joseph Drodge
(74) Attorney, Agent, or Firm—Elias Lambiris; Jason Garbell

(57) ABSTRACT

A microfiltration process of a fermentation-derived product comprising adding activated carbon to a solution of the fermentation-derived product prior to or during the microfiltration process at a microfiltration process temperature of from 25° C. to 65° C.

15 Claims, No Drawings

MICROFILTRATION USING ACTIVATED CARBON

CROSS-REFERENCE TO RELATED APPLICATIONS

This application claims, under 35 U.S.C. 119, priority of Danish application No. PA 2000 00796, filed May 18, 2000, and the benefit of U.S. application No. 60/206,539, filed May 23, 2000, the contents of which are fully incorporated herein by reference.

TECHNICAL FIELD

The present invention relates to a method of increasing process capacity when microfiltrating a fermentation-derived product.

BACKGROUND ART

Microfiltration has been the target for much research and development over the last years. Especially developments in hardware and membranes have been at focus. However two issues still limit the use of microfiltration within recovery of fermented biomolecules. Low fluxes and often also low transmission are the limiting factors for success. Often a process can be developed based on microfiltration for harvest of such products, however in many cases the process will not be able to compete with the more traditional solid liquid separation techniques like centrifugations and drum-filtrations. This is especially the case in continuous large scale processes where fouling necessitates frequent CIP (cleaning-in-place) for maintaining high transmission and flux.

Especially within the biotechnology industry fouling has been an almost unsolvable problem regarding microfiltration of fermentation broths. This is due to the fact that fermentation broths contain besides the product of interest numerous impurities like other intracellular and extracellular metabolites, lysed cells, substrate components, nucleic acids, defoaming agents etc.

Much focus has therefore been allocated to development of hydrophilic membranes and of improved microfiltration hardware with technologies such as back wash/back shock and mechanical induced shear as the more successful developments.

On the operational side focus has been on precise control of trans-membrane pressure and of control of maximum permeate flow rate, as these parameters also are important for limiting membrane fouling. Furthermore, optimisation of process temperature and of pH has also been identified as important parameters for improving the microfiltration performance.

However, even though much development has been going on over the years regarding membranes, hardware and operational parameters, fouling is still today considered the one largest culprit to overcome for developing a successful microfiltration. This is in particular the case for microfiltration of products originating from fermentation broths.

The purpose of this invention is therefore to minimize fouling within microfiltration of fermented products.

SUMMARY OF THE INVENTION

It has surprisingly been found that activated carbon and elevated temperature may increase process capacity when microfiltrating a fermentation-derived product.

Therefore, the present invention provides:

A microfiltration process of a fermentation-derived product comprising adding activated carbon to a solution of the fermentation-derived product prior to or during the microfiltration process at a microfiltration process temperature of from 25° C. to 65° C.

DETAILED DISCLOSURE OF THE INVENTION

The present invention deals with a new and surprisingly effective way of reducing fouling in microfiltration processes of fermentation-derived products.

It has surprisingly been found that fouling can be efficiently minimized in microfiltration processes when activated carbon is added prior to or during the microfiltration step.

It has also been found that a synergy exists between addition of activated carbon and the use of high temperature processing. The performance enhancement by carbon is found to be well suited for the modern microfiltration systems with back wash/back shock and systems with mechanical induced shear.

The use of activated carbon in relation to microfiltration is known from wastewater treatment and also from production of casein hydrolyzate where activated carbon in both cases is used for removing soluble impurities with the aim of improving product quality (WO 93/08702).

However, use of activated carbon with the purpose of minimizing fouling in microfiltration processes has not previously been applied within the biotechnology field.

An added advantage of introducing activated carbon for enhancement of microfiltration performance is that the added carbon in many cases bind unwanted impurities influencing the subsequent concentration or that otherwise needs to be removed by an added purification step for achieving acceptable product quality.

According to the present invention any fermentation-derived product of interest may be microfiltrated as described herein. Especially the method of the invention can be applied to purification of a protein.

In a preferred embodiment, the method is applied to enzymes, in particular to hydrolases (class EC 3 according to Enzyme Nomenclature; Recommendations of the Nomenclature Committee of the International Union of Biochemistry).

In a particular preferred embodiment the following hydrolases are preferred: Proteases: Suitable proteases include those of bacterial or fungal origin. Chemically modified or protein engineered mutants are included. The protease may be a serine protease or a metallo protease, preferably an alkaline microbial protease or a trypsin-like protease. Examples of alkaline proteases are subtilisins, especially those derived from Bacillus, e.g., subtilisin Novo, subtilisin Carlsberg, subtilisin 309, subtilisin 147 and subtilisin 168 (described in WO 89/06279). Examples of trypsin-like proteases are trypsin (e.g. of porcine or bovine origin) and the Fusarium protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235 and 274.

Preferred commercially available protease enzymes include Alcalase™, Savinase™, Primase™, Duralase™, Esperase™, and Kannase™ (Novozymes A/S), Maxatase™, Maxacal™, Maxapem™, Properase™, Purafect™, Purafect OxP™, FN2™, and FN3™ (Genencor International Inc.).
Lipases: Suitable lipases include those of bacterial or fungal origin. Chemically modified or protein engineered mutants are included. Examples of useful lipases include lipases from Humicola (synonym Thermomyces), e.g. from *H. lanuginosa* (*T. lanuginosus*) as described in EP 258 068 and EP 305 216 or from *H. insolens* as described in WO 96/13580, a Pseudomonas lipase, e.g. from *P. alcaligenes* or *P. pseudoalcaligenes* (EP 218 272), *P. cepacia* (EP 331 376), *P. stutzeri* (GB 1,372,034), *P. fluorescens*, Pseudomonas sp. strain SD 705 (WO 95/06720 and WO 96/27002), P. wisconsinensis (WO 96/12012), a Bacillus lipase, e.g. from *B. subtilis* (Dartois et al. (1993), Biochemica et Biophysica Acta, 1131, 253–360), B. stearothermophilus (JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Preferred commercially available lipase enzymes include Lipolase™ and Lipolase Ultra™ (Novozymes A/S). Amylases: Suitable amylases (α and/or β) include those of bacterial or fungal origin. Chemically modified or protein engineered mutants are included. Amylases include, for example, α-amylases obtained from Bacillus, e.g. a special strain of *B. licheniformis*, described in more detail in GB 1,296,839.

Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Commercially available amylases are Duramyl™, Termamyl™, Fungamyl™ and BANT™ (Novozymes A/S), Rapidase™ and Purastar™ (from Genencor International Inc.).
Cellulases: Suitable cellulases include those of bacterial or fungal origin. Chemically modified or protein engineered mutants are included. Suitable cellulases include cellulases from the genera Bacillus, Pseudomonas, Humicola, Fusarium, Thielavia, Acremonium, e.g. the fungal cellulases produced from *Humicola insolens, Myceliophthora thermophila* and *Fusarium oxysporum* disclosed in U.S. Pat. Nos. 4,435,307, U.S. 5,648,263, U.S. 5,691,178, U.S. 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, U.S. 5,686,593, U.S. 5,763,254, WO 95/24471, WO 98/12307 and PCT/DK98/00299.

Commercially available cellulases include Celluzyme™, and Carezyme™ (Novozymes A/S), Clazinase™, and Puradax HA™ (Genencor International Inc.), and KAC-500 (B)™ (Kao Corporation).
Oxidoreductases: Oxidoreductases that may be treated according to the invention include peroxidases, and oxidases such as laccases.
Peroxidases: An enzyme exhibiting peroxidase activity may be any peroxidase enzyme comprised by the enzyme classification (EC 1.11.1.7), or any fragment derived therefrom, exhibiting peroxidase activity.

Preferably, the peroxidase employed in the method of the invention is producible by microorganisms such as fungi or bacteria. Some preferred fungi include strains belonging to the subdivision Deuteromycotina, class Hyphomycetes, e.g., Fusarium, Humicola, Tricoderma, Myrothecium, Verticillum, Arthromyces, Caldariomyces, Ulocladium, Embellisia, Cladosporium or Dreschlera, in particular *Fusarium oxysporum* (DSM 2672), *Humicola insolens, Trichoderma resii, Myrothecium verrucana* (IFO 6113), *Verticillum alboatrum, Verticillum dahlie, Arthromyces ramosus* (FERM P-7754), *Caldariomyces fumago, Ulocladium chartarum, Embellisia alli* or *Dreschlera halodes*.

Other preferred fungi include strains belonging to the subdivision Basidiomycotina, class Basidiomycetes, e.g. Coprinus, Phanerochaete, Coriolus or Trametes, in particular *Coprinus cinereus* f. microsporus (IFO 8371), *Coprinus macrorhizus, Phanerochaete chrysosporium* (e.g. NA-12) or Trametes (previously called Polyporus), e.g. *T. versicolor* (e.g. PR4 28-A).

Further preferred fungi include strains belonging to the subdivision Zygomycotina, class Mycoraceae, e.g. Rhizopus or Mucor, in particular *Mucor hiemalis*.

Some preferred bacteria include strains of the order Actinomycetales, e.g., *Streptomyces spheroides* (ATTC 23965), *Streptomyces thermoviolaceus* (IFO 12382) or *Streptoverticillum verticillium* ssp. *verticillium*.

Other preferred bacteria include Bacillus pumilus (ATCC 12905), *Bacillus stearothermophilus, Rhodobacter sphaeroides, Rhodomonas palustri, Streptococcus lactis, Pseudomonas purrocinia* (ATCC 15958) or *Pseudomonas fluorescens* (NRRL B-11).

Further preferred bacteria include strains belonging to Myxococcus, e.g., *M. virescens*.

Particularly, a recombinantly produced peroxidase is preferred, e.g., a peroxidase derived from a Coprinus sp., in particular *C. macrorhizus* or *C. cinereus* according to WO 92/16634, or a variant thereof, e.g., a variant as described in WO 93/24618 and WO 95/10602.
Laccases and Laccase Related Enzymes: In the context of this invention, laccases and laccase related enzymes contemplate any laccase enzyme comprised by the enzyme classification (EC 1.10.3.2), any chatechol oxidase enzyme comprised by the enzyme classification (EC 1.10.3.1), any bilirubin oxidase enzyme comprised by the enzyme classification (EC 1.3.3.5) or any monophenol monooxygenase enzyme comprised by the enzyme classification (EC 1.14.18.1).

The microbial laccase enzyme may be derived from bacteria or fungi (including filamentous fungi and yeasts) and suitable examples include a laccase derivable from a strain of Aspergillus, Neurospora, e.g., *N. crassa*, Podospora, Botrytis, Collybia, Fomes, Lentinus, Pleurotus, Trametes, e.g., *T. villosa* and *T. versicolor*, Rhizoctonia, e.g., *R. solani*, Coprinus, e.g. *C. plicatilis* and *C. cinereus*, Psatyrella, Myceliophthora, e.g. *M. thermophila*, Schytalidium, Polyporus, e.g., *P. pinsitus*, Phlebia, e.g., *P. radita* (WO 92/01046), or Coriolus, e.g., *C. hirsutus* (JP 2-238885), in particular laccases obtainable from Trametes, Myceliophthora, Schytalidium or Polyporus.

Other preferred hydrolases are carbohydrolases, transferases, lyases, isomerases, and ligases.

The method of the invention may be applied to an untreated fermentation broth or to a fermentation broth that has first been subjected to, e.g., a pH adjustment, a temperature adjustment, a water dilution and/or one or more solid/liquid separatory techniques such as flocculation or centrifugation.

According to the present invention a microfiltration process means a membrane filtration separating soluble products from solids such as biomass and other particulate matter. Any membrane equipment known in the art may be used, but it is preferred that the membrane filtration is done using membrane techniques such as hollow fiber, tubular, or plate and frame units. The membranes may be made of a variety of materials such as polysulfone membranes (PS) or teflon (PTFE). The preferred cut off value will depend on the properties of the fermentation-derived product in question but usually a cut off value in the interval of from 200 kD to a pore size of 2 μm is preferred.

According to the present invention activated carbon means any activated carbon known in the art; useful activated carbon types may be Acticarbon 4S #2228, available from Elf Atochem North America; Darco carbon KB-B, available from American Norit Co.; Calgon granular carbon, available from Pittsburgh Activated Carbon; or Picatif FGV 120, available from Pica, France.

According to the present invention the added amount of carbon is preferably from 0.05 to 2% (w/w) of the initial fermentation broth volume, in particular the added amount of carbon is from 0.1 to 1% (w/w) of the initial fermentation broth volume.

According to the present invention the microfiltration process is preferably carried out at a temperature of from 25° C. to 65° C.; preferably at a temperature of from 30° C. to 60° C.; more preferably at a temperature of from 30° C. to 55° C.; especially at a temperature of from 35° C. to 50° C.

If a pH adjustment is necessary any acid or base may be used, but formic acid or acetic acid are preferred as acids, and sodium hydroxide is preferred as base. The optimal pH is normally a compromise between the pH at which the fermentation-derived product of interest is most stable and the pH at which the solubility of the fermentation-derived product of interest is greatest.

The microfiltration process may be further improved if in addition to the carbon treatment an Al-product is added (see Example 3). The Al-product may be added to the fermentation broth prior to or during the microfiltration process.

According to the invention any soluble Al compound or any mixture thereof may be used, in particular $Al_2(SO_4)_3$, $NaAlO_2$, $Na_2Al_2O_4$, $K_2Al_2O_4$, $Al(NO_3)_3$, $AlCl_3$, Al-acetate, Al-formate, or polymer aluminiumhydroxychloride (e.g., EKOFLOCK available from Boliden).

According to the present invention the added amount of the Al-product is preferably from $1.4 \times 10^{-3}$ to $2.8 \times 10^{-1}$ (mol Al/w) of the initial fermentation broth volume, in particular the added amount of the Al-product is from $1.4 \times 10^{-2}$ to $1.4 \times 10^{-1}$ (mol Al/w) of the initial fermentation broth volume.

The microfiltration process may be further improved if in addition to the carbon treatment a Ca-product is added (see Example 4). The Ca-product may be added to the fermentation broth prior to or during the microfiltration process.

According to the invention any soluble Ca compound or any mixture thereof may be used, in particular $CaSO_4$, $Ca(OH)_2$, or $CaCl_2$.

According to the present invention the added amount of the Ca-product is preferably from $1.6 \times 10^{-2}$ to $4.9 \times 10^{-1}$ (mol Ca/w) of the initial fermentation broth volume, in particular the added amount of the Ca-product is from $3.2 \times 10^{-2}$ to $3.2 \times 10^{-1}$ (mol Ca/w) of the initial fermentation broth volume.

The microfiltration process may be even further improved if in addition to the carbon treatment an Al-product and a Ca-product are added.

It should also be noted that the microfiltration process according to the present invention may be a batch process or a continuous process.

The fermentation-derived product achieved according to the invention may be further purified in a variety of ways such as by using ultrafiltration, evaporation, chromatographic methods, adsorption and/or crystallization processes.

The invention is further illustrated in the following examples which are not intended to be in any way limiting to the scope of the invention as claimed.

EXAMPLE 1

Trial set-up: batches of 150 liter of Savinase broth, fermented e.g. as described in U.S. Pat. No. 3,723,250, were diluted to 225 liter, pH was adjusted to 6.0 and the solutions were microfiltered on a 3.7 $m^2$ PallSep PS 400 VMF module (0.45 μm PTFE) with a transmembrane pressure of 0.4 bar and with 300 liter diafiltration water.

| Trial # | Carbon addition (Picatif FGV 120) | Process Temperature | Yield | Flux |
|---|---|---|---|---|
| 1 | 0% | 20° C. | 85% | 17 l/$m^2$ * hr |
| 2 | 0.2% | 20° C. | 87% | 19 l/$m^2$ * hr |
| 3 | 0% | 40° C. | 86% | 27 l/$m^2$ * hr |
| 4 | 0.2% | 40° C. | 86% | 32 l/$m^2$ * hr |

As can be seen from the experiments above the addition of activated carbon has a large influence on process capacity and furthermore, there seems to be a synergistic effect on capacity when combining carbon addition with high temperature processing: At 20° C., when 0.2% activated carbon is added, there is an increase in flux of $(19-17)/17 \times 100\% = 12\%$; At 40° C., when 0.2% activated carbon is added, there is an increase in flux of $(32-27)/27 \times 100\% = 19\%$.

As process time between each CIP is of large importance for overall process economy and as fouling problems are particular problematic within microfiltration of fermentation-derived products, the ability of carbon for avoiding long time fouling problems was examined.

For this study a protein-engineered variant of Savinase was chosen (Kannase), fermented in the same way as in the previous 4 trials. In this case 2 $m^3$ fermentation broth was diluted to 3 $m^3$, pH was adjusted to 6.0 and 4.0 kg of carbon Picatif FGV 120 was added. The microfiltration was performed at 30° C. and transmission and flux were measured during the experiment.

| Results: | |
|---|---|
| Transmission (start): | 95% |
| Transmission (1 hr): | 95% |
| Transmission (4 hr): | 95% |
| Transmission (7 hr–end): | 95% |
| Flux (start): | 22 (l/$m^2$ * hr) |
| Flux (1 hr): | 23 (l/$m^2$ * hr) |
| Flux (4 hr): | 24 (l/$m^2$ * hr) |
| Flux (7 hr–end): | 24 (l/$m^2$ * hr) |

It can be seen from the results given above that there was no decrease in either the transmission or in the membrane flux over the total trial period.

EXAMPLE 2
Trial Set-up for Termamyl (Amylase)

A volume of 150 kg Termamyl broth, fermented as described in GB 1,296,839, was diluted to 310 liter with water and 0.300 kg of carbon Picatif FGV 120 together with 6.9 kg of a 45% (w/w) solution of $Na_2Al_2O_4$ from Nordisk Aluminat. pH was adjusted to 10.6, and the microfiltration was done in a continuous mode at 45° C. and 60° C. The solutions were microfiltered on a 1 m2 PallSep PS 10 VMF module (0.45 μm PTFE) and at a TMP (transmembrane pressure) equal or below 0.4 Bar. Average permeabilities were calculated as explained below:

To obtain a better comparison between the continuous filtration experiments by eliminating any minor differences in TMP, the average permeability has been calculated as follows: Permeability=Flux/TMP (Flux=permeability× TMP). The permeability is a measurement of the amount of fouling, e.g. the higher the permeability the smaller the amount of fouling the better pre-treatment method or filtration process.

| Trial | Process temperature | Permeability L/(m² * hr * bar) |
|---|---|---|
| 1 | 45° C. | 138 |
| 2 | 60° C. | 157 |

EXAMPLE 3
Trial Set-up for the Addition of Sodium Aluminate to a Savinase Broth A Savinase broth, fermented as described above, was divided up in 4 parts. To each part 100% water was added together with 0.2% carbon (Picatif FGV 120), and the pH was adjusted to 5.2. A 45% solution of Sodium Aluminate ($Na_2Al2O_4$) from Nordisk Aluminat was added as 0.77% (w/w), 1.54%(w/w) and 3.1% (w/w) to three of the four prepared solutions. The solutions were microfiltered on a 1 m² PallSep PS 10 VMF module (0.45 μm PTFE) in a continuous mode at 40° C. and at a TMP equal or below 0.4 Bar. Average permeabilities are compared as explained above.

| Contents | Solution 1 (reference) | Solution 2 (0.77% Sodium Aluminate) | Solution 3 (1.54% Sodium Aluminate) | Solution 4 (3.10% Sodium Aluminate) |
|---|---|---|---|---|
| Broth | 140 kg | 125 kg | 90 kg | 60 kg |
| Water | 140 kg | 125 kg | 90 kg | 60 kg |
| Carbon | 0.280 kg | 0.250 kg | 0.180 kg | 0.120 kg |
| $Na_2Al_2O_4$ (45%) (or as mol Al) | — | 0.96 kg (2.63 mol) | 1.39 kg (3.80 mol) | 1.86 kg (5.10 mol) |

The result from the trials were as follows:

| Solution | Sodium Aluminate | Permeability l/(m² * hr * bar) |
|---|---|---|
| 1 | 0.00% | 107 |
| 2 | 0.77% | 136 |
| 3 | 1.54% | 132 |
| 4 | 3.10% | 170 |

EXAMPLE 4
Trial Set-up for the Addition of CaCl2 to Savinase Broth

A Savinase broth, fermented as described above, was divided up in 5 parts. To each part 100% water was added together with 0.2% carbon (Picatif FGV 120), and the pH was adjusted to 5.2. A 36% solution of $CaCl_2$ was added to the 5 solutions as 2.00% (w/w), 4.00%(w/w), 6.0% (w/w) 8.0% (w/w) and 12% (w/w). The 5 Calcium Chloride treated solutions were microfiltered on a 1 m² PallSep PS 10 VMF module (0.45 μm PTFE) in a continuous mode at 40° C. at a TMP equal or below 0.4 Bar. Average permeabilities are compared as explained above.

| Contents | Solution A (2.00% $CaCl_2$) | Solution B (4.00% $CaCl_2$) | Solution C (6.00% $CaCl_2$) | Solution D (8.0% $CaCl_2$) | Solution E (12.0% $CaCl_2$) |
|---|---|---|---|---|---|
| Broth | 150 kg | 100 kg | 50 kg | 100 kg | 57.5 kg |
| Water | 150 kg | 100 kg | 50 kg | 100 kg | 57.5 kg |
| Carbon | 0.300 kg | 0.200 kg | 0.100 kg | 0.200 kg | 0.116 kg |
| $CaCl_2$ (36%) (or as mol Ca) | 3.00 kg (9.73 mol) | 4.00 kg (12.97 mol) | 3.00 kg (9.73 mol) | 8.00 kg (25.95 mol) | 6.90 kg (22.46 mol) |

The result from the trials were as follows:

| Solution | $CaCl_2$ (36%) | Permeability l/m² * hr * bar |
|---|---|---|
| A | 2.00% | 183 |
| B | 4.00% | 202 |
| C | 6.00% | 229 |
| D | 8.00% | 220 |
| E | 12.00% | 215 |

What is claimed is:

1. A microfiltration process of a fermentation-derived product comprising adding activated carbon to a solution of the fermentation-derived product prior to or during the microfiltration process at a microfiltration process temperature of from 25° C. to 65° C.

2. A process according to claim 1, wherein the fermentation-derived product is a protein.

3. A process according to claim 1, wherein the fermentation-derived product is an enzyme.

4. A process according to claim 1, wherein the fermentation-derived product is a protease, an amylase or a cellulase.

5. A process according to claim 1, wherein the microfiltration temperature is from 30° C. to 60° C.

6. A process according to claim 1, wherein the microfiltration temperature is from 30° C. to 55° C.

7. A process according to claim 1, wherein the microfiltration temperature is from 35° C. to 50° C.

8. A process according to claim 7, wherein the added amount of carbon is from 0.1 to 1% (w/w) of the initial fermentation solution volume.

9. A process according to any of the claims 1–7 wherein the added amount of carbon is from 0.05 to 2% (w/w) of the initial fermentation solution volume.

10. A process according to claim 1, wherein additionally an Al-product is added to the solution prior to or during the microfiltration process.

11. A process according to claim 10, wherein the added amount of the Al-product is from $1.4 \times 10^{-3}$ to $2.8 \times 10^{-1}$ (mol Al/w) of the initial fermentation solution volume.

12. A process according to claim 1, wherein additionally a Ca-product is added to the solution prior to or during the microfiltration process.

13. A process according to claim 12, wherein the added amount of the Ca-product is from $1.6 \times 10^{-2}$ to $4.9 \times 10^{-1}$ (mol Ca/w) of the initial fermentation solution volume.

14. A process according to claim 1, wherein additionally an Al-product and a Ca-product are added to the solution prior to or during the microfiltration process.

15. A process according to claim 1, wherein the microfiltration process is a batch process or a continuous process.

* * * * *